US010151737B2

(12) United States Patent
Li et al.

(10) Patent No.: US 10,151,737 B2
(45) Date of Patent: Dec. 11, 2018

(54) METHOD FOR PERMEABILITY PREDICTION OF SHALE GAS (71) Applicant: KING FAHD UNIVERSITY OF PETROLEUM AND MINERALS, Dhahran (SA)

(72) Inventors: Jun Li, Dhahran (SA); Abdullah S. Sultan, Dhahran (SA)

(73) Assignee: KING FAHD UNIVERSITY OF PETROLEUM AND MINERALS, Dhahran (SA)

(*) Notice: Subject to any disclaimer, the term of this patent is extended or adjusted under 35 U.S.C. 154(b) by 165 days.

(21) Appl. No.: 14/990,411

(22) Filed: Jan. 7, 2016

(65) Prior Publication Data
US 2016/0299117 A1 Oct. 13, 2016

Related U.S. Application Data (60) Provisional application No. 62/144,154, filed on Apr. 7, 2015.

(51) Int. Cl.
*G01N 33/24* (2006.01)
*E21B 49/00* (2006.01)
(52) U.S. Cl.
CPC ............ *G01N 33/24* (2013.01); *E21B 49/00* (2013.01)
(58) Field of Classification Search
None
See application file for complete search history.

(56) References Cited

U.S. PATENT DOCUMENTS

| | | | | |
|---|---|---|---|---|
| 5,172,717 A | * | 12/1992 | Boyle | E21B 34/06 137/155 |
| 9,201,026 B2 | * | 12/2015 | Walls | G01N 23/22 |
| 9,507,047 B1 | * | 11/2016 | Dvorkin | G01V 5/101 |
| 2010/0096128 A1 | * | 4/2010 | Hinkel | E21B 43/16 166/270.1 |
| 2012/0101787 A1 | * | 4/2012 | Zhou | E21B 43/00 703/2 |
| 2013/0259190 A1 | * | 10/2013 | Walls | G01N 23/22 378/9 |
| 2014/0054032 A1 | * | 2/2014 | Affholter | E21B 43/24 166/272.6 |

(Continued)

OTHER PUBLICATIONS

Civan, F., "Scale Effect on Porosity and Permeability: Kinetics, Model, and Correlation", AIChE Journal, vol. 47, No. 2, Feb. 2001, pp. 272-287.*

(Continued)

*Primary Examiner* — Joseph Schoenholtz
(74) *Attorney, Agent, or Firm* — Oblon, McClelland, Maier & Neustadt, L.L.P.

(57) ABSTRACT

This disclosure relates to a system and method for applying a prediction of permeability of shale gas in porous media at different pressure conditions to a shale gas production. The method uses a molecular model that accounts for slippage and adsorption effects under the different pressure conditions including simulated gas flows in a large computational domain representing a sample of shale rock. This system and method provides a computationally efficient processing to determine permeability variations of shale gas with the different pressure conditions.

5 Claims, 6 Drawing Sheets

(56) References Cited

U.S. PATENT DOCUMENTS

| | | | |
|---|---|---|---|
| 2015/0345258 A1* | 12/2015 | Sanborn | E21B 41/005 |
| | | | 166/311 |
| 2016/0047179 A1* | 2/2016 | Kjorholt | E21B 43/255 |
| | | | 166/308.1 |
| 2018/0003786 A1* | 1/2018 | Washburn | G01R 33/44 |
| 2018/0016897 A1* | 1/2018 | Willberg | E21B 43/26 |

OTHER PUBLICATIONS

Li, J., "Efficiency and Stability of the SDBGK Model", 28 International Symposium on Rarefied Gas Dynamics, 2012, API Conf. Proc. 1501, pp. 849-856.*

Ambrose, Raymond J., et al. "Shale Gas-in-Place Calculations Part I: New Pore-Scale Considerations." SPE Journal, vol. 17, No. 01, 2012, pp. 219-229., doi:10.2118/131772-pa.*

Sheng, M., et al., "Shale-Gas Permeability Model with Effects of Multiscale Flow based on Fractal Pore Space Geometry", URL: http://www.researchgate.net/publication/270956204_Shale-gas_permeability_model_with_effects_of_multiscale_flow_based_on_fractal_pore_space_geometry, Research Gate, 19 Pages total, (Dec. 2014).

Taitano, W., et al., "Moment-Based Acceleration for Neutral Gas Kinetics with BGK Collision Operator", URL: http://www.researchgate.net/publication/271749235_Moment-Based_Acceleration_for_Neutral_Gas_Kinetics_with_BGK_Collision_Operator, Journal of Computational and Theoretical Transport, vol. 43, No. 1-7, 1 Page total, (Dec. 2014) (Abstract only).

Ching, S., et al., "Direct Numerical Test of the B-G-K Model Equation by the DSMC Method", URL: http://link.springer.com/article/10.1007/BF02486705, Acta Mechanica Sinica (English Series), vol. 16, No. 2, 5 Pages total, (May 2000).

Li, J., "Improved Diffuse Boundary Condition for the DSBGK Method to Eliminate the Unphysical Density Drift", URL: https://www.researchgate.net/publication/260873089_Improved_Diffuse_Boundary_Condition_for_the_DSBGK_Method_to_Eliminate_the_Unphysical_Density_Drift, Research Gate, 13 Pages total, (Mar. 18, 2014).

Li, J., "Comparison between the DSMC and DSBGK Methods", URL: https://www.researchgate.net/publication/228115686_Comparison_between_the_DSMC_and_DSBGK_Methods, Research Gate, 34 Pages total, (Jul. 5, 2012).

Li, J., "Efficiency and Stability of the DSBGK Method", URL: http://scitation.aip.org/content/aip/proceeding/aipcp/10.1063/1.4769631?ver=pdfcov, AIP Conference Proceedings, vol. 1501, No. 849, 9 Pages total, (2012).

Li, J., "Direct Simulation Method Based on BGK Equation", AIP Conference Proceedings, vol. 1333, No. 1, 6 Pages total, (May 2011).

Civan, F., et al., "Shale-Gas Permeability and Diffusivity Inferred by Improved Formulation of Relevant Retention and Transport Mechanisms", Transport in Porous Media, vol. 86, pp. 925-944, (2011).

Sakhaee-Pour, A., "Gas Flow Through Shale", The University of Texas at Austin, 202 Pages total, (Aug. 2012).

Klinkenberg, L.J., "The Permeability of Porous Media to Liquids and Gases", URL: https://www.onepetro.org/conference-paper/API-41-200, Drilling and Production Practice, 2 Pages total, (1941) (Abstract only).

Sakhaee-Pour, A., et al., "Gas Permeability of Shale", URL: https://www.onepetro.org/journal-paper/SPE-146944-PA, SPE Reservoir Evaluation & Engineering, vol. 15, No. 4, 3 Pages total, (Aug. 2012) (Abstract only).

Ambrose, R.J., et al., "New Pore-Scale Considerations for Shale Gas in Place Calculations", URL: https://www.onepetro.org/conference-paper/SPE-131772-MS, SPE Unconventional Gas Conference, 2 Pages total, (2010) (Abstract only).

* cited by examiner

FIG. 1A

SHALE GAS PRODUCTION SYSTEM

METHOD FOR PERMEABILITY PREDICTION OF SHALE GAS

CROSS-REFERENCE TO RELATED APPLICATIONS

This application claims the benefit of U.S. Provisional Application 62/144,454, filed Apr. 7, 2015, which is incorporated herein by reference in its entirety.

FIELD OF THE INVENTION

The field of this invention relates to shale gas production and applied computational methods.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Productive reservoir systems of shale gas are composed of four types of porous media: inorganic matrix, organic matrix, natural fractures, and hydraulically induced fractures. Numerous organic flakes are sparsely scattered inside the inorganic matrix and are intersected by the natural fractures. Computational methods may be used to predict and enhance shale gas production from shale deposits, where permeability of the porous media is an important input parameter. Factors including a slippage effect and an adsorption affect permeability at nano and micro scales, which results in traditional computational methods that are either computationally too time consuming or require significant simplifications, thereby sacrificing accuracy and increasing errors.

Accounting for the slippage effect at high Knudsen (Kn) number is challenging in pore-scale simulations to accurately compute the permeability, therefore it has been treated using empirical correlation models to estimate the permeability of shale gas in shale deposits. Generally, permeability increases with the Kn number. The Kn number is defined here as the ratio of molecular mean free path to the representative pore size of shale rock. The Kn number is usually large in the organic matrix due to nano-pores. The molecular mean free path increases with decrease of pressure and thus permeability increases correspondingly during the gas production process.

Adsorption effect at a pore surface is also remarkable in shale gas flows due to nano-pores. The adsorption effect results in an adsorption thickness on the pore surface, which depends on the pressure and material of the pore surface. When the adsorption thickness is alike to the pore size of shale rock, the permeability significantly decreases due to a reduction of effective passage area. In contrast, the slippage effect at high Kn increases the permeability and also depends on the pressure as discussed above. Consequently, the prediction of permeability variation with pressure is very difficult due to the slippage and adsorption effects. Traditional experimental scheme to measure the flow speed to determine the permeability of shale gas requires considerable time and is usually subjected to noises and errors due to low flow speed. Transient pressure decay is measured in the current pulse-decay experimental scheme and applied in a mathematical model to inversely predict the permeability of the shale rock sample. But, this scheme is not convincible because of being dependent on an empirical correction term at high Kn obtained with significant simplifications.

SUMMARY OF THE INVENTION

This disclosure relates to a system and method for numerically predicting permeability of shale gas in porous media at different pressure conditions, as well as for shale gas production. The method uses a molecular model that accounts for the slippage and adsorption effects under different pressure conditions including simulated gas flows in a large computational domain representing a sample of shale rock. This system and method provides computationally efficient processing to determine permeability variation of shale gas with different pressure conditions.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

This disclosure relates to a system based on a Direct Simulation Method Based on Bhatnagar-Gross-Krook Equation (DSBGK method) applied for permeability prediction of shale gas, as well as for shale gas production. A computational domain is created to represent a pore-scale geometry of a shale rock sample with consideration of the adsorption effect by adjusting an effective pore space according to an adsorption layer thickness. The computational domain is divided into a plurality of cells having a set of cell boundaries and a set of cell variables. The plurality of cells further contain a distribution of molecules having a set of molecular variables that are distributed within the effective pore space of the shale rock sample.

The method disclosed here uses a plurality of time steps to update the cell variables using the plurality of increments of molecular variables based on mass, momentum and energy conservation principles of intermolecular collision processes. As an example, a two-dimensional benchmark problem is utilized to model the permeability as a function of pressure. This method significantly reduces noise because the molecular variables are updated smoothly by an extrapolation of an acceptance-rejection scheme and thus the increments contain low noise. Details on design of the scheme are further described herein.

The application of the DSBGK method to predict shale gas permeability with consideration of the slippage effect in shale gas systems has first been introduced by the inventors in their recent publications: Li J., Sultan A., Klinkenberg Slippage Effect in the Permeability Computations of Shale Gas by the Pore-scale Simulations, eprint arXiv: 1505.01781, physics.flu-dyn, 2015 and Li J., Sultan A., Permeability Computations of Shale Gas by the Pore-scale Monte Carlo Molecular Simulations, IPTC-18263-MS, 2015, which are herein incorporated by reference.

Gas flow problems at different scales need different theoretical descriptions. If a pore size is alike to a molecular mean free path but much larger than a molecular size of surrounding fluid molecules, a flow phenomenon and boundary condition can be described by statistical models.

Deterministic models, like the molecular dynamics (MD) method, become necessary only if the pore size is alike to the molecular size of the fluid molecules. In the case of shale gas, a pore with a size alike to a methane molecule is usually blocked due to adsorption and so the pores are negated in the computation of permeability. Thus, statistical models are valid in the simulations of pore-scale flows to compute the permeability of shale gas.

The gas flow can be divided into different regimes according to Kn: 1) continuum regime with Kn<0.01, where the Navier-Stokes (N-S) equation and the no-slip boundary condition are valid; 2) slip regime with 0.01<Kn<0.1, where a slip boundary condition should be used with the N-S equation; 3) transitional regime 0.1<Kn<10, where the Boltzmann equation at the molecular level in a statistical way is necessary; 4) free molecular flow regime 10<Kn, where the Boltzmann equation is significantly simplified and sometimes the analytical solutions are available. The operating range of productive shale gas usually covers the slip and the transitional regimes. Compared to the pore-scale gas flow in a reservoir with large pore size and thus small Kn, the adsorption and the slippage effects at the pore surface are remarkable in the shale gas flows due to small pore size.

Figure 1A:
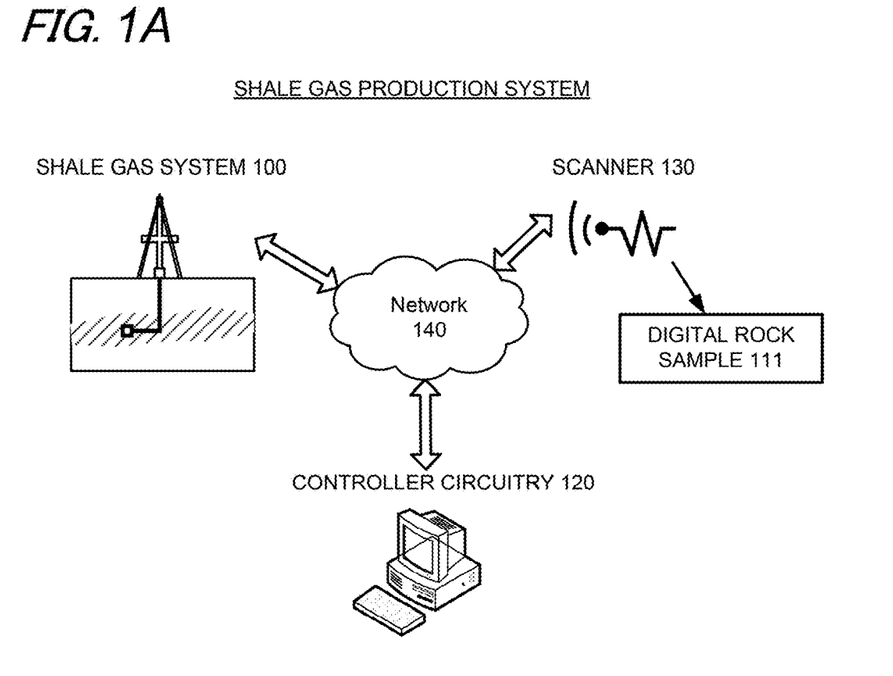
FIG. 1A shows a shale gas production system diagram according to an example.

FIG. 1A shows an example of a shale gas production system including a shale gas system 100 in communication with a scanner 130, which are both in communication with a controller circuitry 120 by a network 140. The network 140 can be any network or circuitry that allows the shale gas system 100, the scanner 130, and the controller circuitry 120 to communicate with each other. The scanner 130 is configured to create a digital rock sample 111 or spatial representation of a shale rock sample. For examples the scanner 130 may be one of a Focused Ion Beam Scanning Electron Microscope (FIB/SEM), an ultrasonic sensor system, or any other sensing system that can spatially digitize the shale rock sample with a pore-scale resolution. Other examples of the scanner 130 can include porosity evaluation tools used in acoustic logging, which is based on a comparison of a compressional velocity of sound in fluid and in rock. In one embodiment, the scanner 130 can operate with the shale rock sample in situ.

The network 140 may include the Internet or any other medium capable of communicating data between devices. Suitable networks can include or interface with any one or more of a local intranet, a PAN (Personal Area Network), a LAN (Local Area Network), a WAN (Wide Area Network), a MAN (Metropolitan Area Network), a VPN (Virtual Private Network), or a SAN (storage area network). Furthermore, communications may also include links to any of a variety of wireless networks, including WAP (Wireless Application Protocol), GPRS (General Packet Radio Service), GSM (Global system for Mobile Communication), CDMA (Code Division Multiple Access) or TDMA (Time Division Multiple Access), cellular phone networks, GPS (Global Positioning System), CDPD (Cellular digit packet data), Bluetooth radio, or an IEEE 802.11 based radio frequency. As can be appreciated, the network 140 can be a public network, such as the Internet, or a private network such as an LAN or WAN network, or any combination thereof and can also include PSTN or ISDN sub-networks. The network 140 can also be wireless such as a cellular network including EDGE, 3G and 4G wireless cellular systems. The wireless network can also be WiFi, Bluetooth, or any other wireless form of communication that is known.

In an alternate example, the communication done by the network 140 can be substituted with any transferable data medium such as CDs, DVDs, in FLASH memory, RAM, ROM, PROM, EPROM, EEPROM, hard disk or any other information processing device with which the network 140 communicates, such as a server or computer.

Figure 1B:
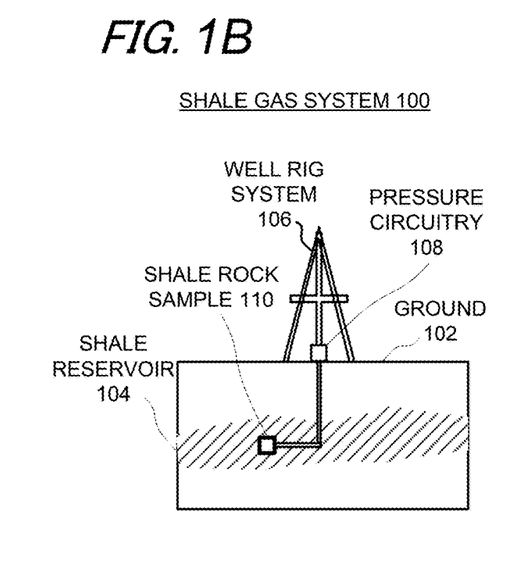
FIG. 1B shows a shale gas system diagram according to an example.

FIG. 1B shows an example of the shale gas system 100 including a well rig system 106 having piping that penetrates a shale reservoir 104 in a ground location 102 and hydraulics that apply a pressure to extract a gas.

The well rig system 106 includes any heavy machinery equipment, corers, chemicals, proppants, and fluids that are used in production of shale gas. The well rig system 106 can include mobile equipment mounted on trucks, tracks or trailers, or more permanent land or marine-based structures such as oil platforms, commonly called 'offshore oil rigs' even if they don't contain a drilling rig. The term "rig" therefore generally refers to any complex of equipment that is used to penetrate a surface of the Earth's crust. In one example, the well rig system 106 can include different systems for creating a borehole into the shale reservoir 104, obtaining a rock sample, and for producing shale gas. The well rig system 106 further includes a pressure circuitry 108 to adjust the pressure applied to the shale reservoir 104. The well rig system 106 can include other devices, methods, and systems known to those in the art of shale gas production.

A sample of the shale reservoir 104 is a shale rock sample 110, which has a combination of different types of a porous media including solid and void mediums, and therefore has porosity. The shale rock sample 110 can be extracted from the shale reservoir 104 by several scenarios commonly known to those in the art of core bowling. A rock sample can be taken from the borehole of the shale reservoir 104 with its long axis oriented roughly parallel to the axis of the borehole, or parallel to the gravity field for the gravity-driven tools. In the case of horizontal drilling, rock samples having other orientations can be taken. Specific drills can be used such as a rotary drill using diamond drill bits and a triple tube wire-line system as needed.

The digital rock sample 111 obtained or created by the scanner 130 is received by the controller circuitry 120, where the DSBGK method is executed to compute the permeability at different pressure conditions.

Figure 1C:
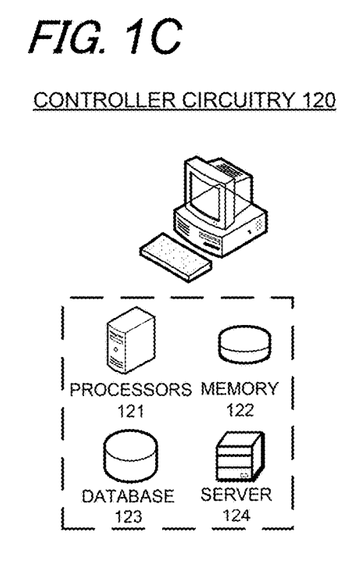
FIG. 1C shows a controller circuitry diagram according to an example.

FIG. 1C shows an example of the controller circuitry 120. The controller circuitry 120 may be configured to control the pressure circuitry 108 of the well rig system 106, and thereby control the pressure used during a shale gas production process. In an alternative example, the pressure circuitry 108 is part of the controller circuitry 120.

The controller circuitry 120 includes software that may be configured to communicate and to control the shale gas system 100 and the pressure circuitry 108, to send or receive data representing the digital rock sample 111 or the shale rock sample 110, and to process the methods further described herein. The hardware elements in order to perform the method described herein may be realized by various machinery and circuitry elements. The controller circuitry 120 may include different hardware components including one or more processors 121, memory 122, a database 123, and a server 124, which can be in one workstation or a high performance computing (HPC) system. The controller circuitry 120 can be circuitry, such as a processing circuitry that is configured to execute one or more sequences of one or more instructions contained in a memory 122. The one or more processors 121 in a multi-processing arrangement may also be employed to execute the sequences of instructions contained in the memory 122. In alternative examples, hard-wired circuitry may be used in place of or in combination with software instructions. Thus, embodiments are not limited to any specific combination of hardware circuitry and software.

In an exemplary embodiment, a personal laptop configured to run Fortran MPI computer code may be used. In another example, the HPC system configured for solving large-scale problems may be used. The HPC may utilize distributed computing such as in grid computing, where the instructions are implemented with multiple processors 121 cooperatively working in parallel or in serial to perform the set of instructions of the inventive processes described herein. The process data and the computer code, the software, or set of instructions may be stored in the memory 122 or on CDs, DVDs, in FLASH memory, RAM, ROM, PROM, EPROM, EEPROM, hard disk or any other information processing device with which any part of the controller circuitry 120 communicates.

Figure 2A:
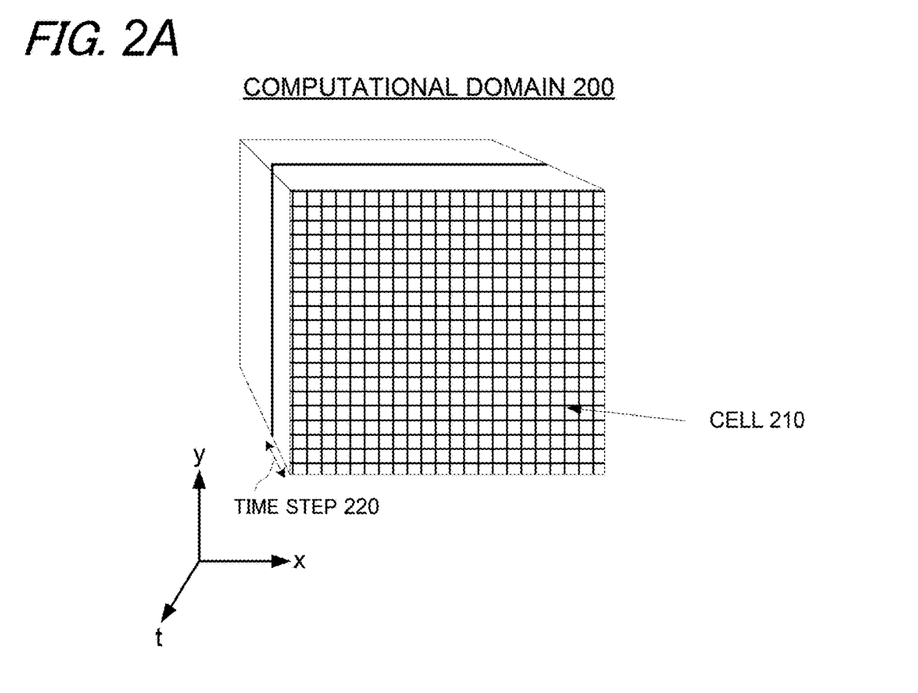
FIG. 2A shows a computational domain divided into a number of cells and a simulation process divided into a series of time steps according to an example.

FIG. 2A shows a computational domain 200 divided into a number of cells 210 and the simulation process is divided into a number of ordered time steps 220 ($\Delta t$) according to an exemplary embodiment. The division of the computational domain 200 maintains a spatial order and organization of the cells 210 in the x-direction and y-direction.

Figure 2B:
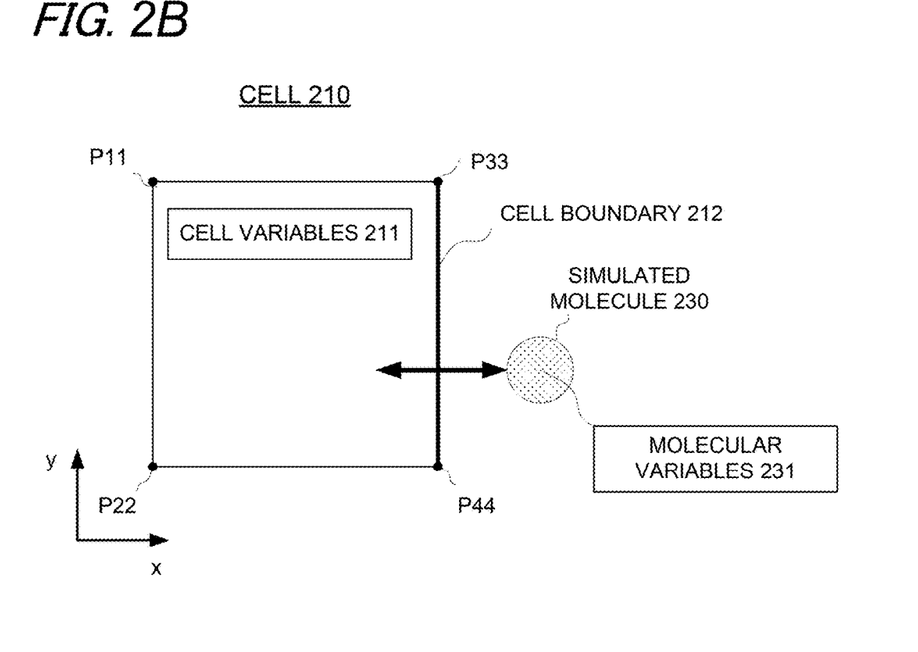
FIG. 2B shows an example of a void cell containing few simulated molecules.

FIG. 2B shows an example of a cell 210 having a set of cell variables 211 and a set of cell boundaries 212, and one or more simulated molecules 230 that can move in and out of the cell 210 during each time step 220. The cell variables 211 include a number density n, a flow velocity u, and a temperature T. Each simulated molecule 230 has a set of molecular variables 231, including a spatial position, a molecular velocity, a number N of real molecules that are represented by the simulated molecule 230, and a probability distribution function F. Each cell boundary 212 includes one or more of a set of cell boundary conditions, such as a temperature T and a pressure p for an open boundary condition and the diffuse reflection model for a solid boundary condition.

In this example, the cell boundaries 212 may be described by a set of points P11, P22, P33, and P44 of the cell 210. A combination of more than one cell boundary 212 may have relative properties. For example, the cell boundary 212 defined by points P11 and P22 may be considered as an inlet having a fixed pressure $p_0$ and the cell boundary 212 defined by points P33 and P44 may be considered as an outlet having a fixed pressure equal to $p_0-\Delta p_0$, where $\Delta p_0$ is a pressure difference between the two cell boundaries 212. In a preferred embodiment, the pressure difference between the two cell boundaries 212 in the x-direction drives a flow in the x-direction. In this example, the molecule is a methane molecule having a molecular mass m=26.63×10$^{-27}$ kg and a viscosity $\mu$=1.024×10$^{-5}$ Pa·s.

Figure 3A:
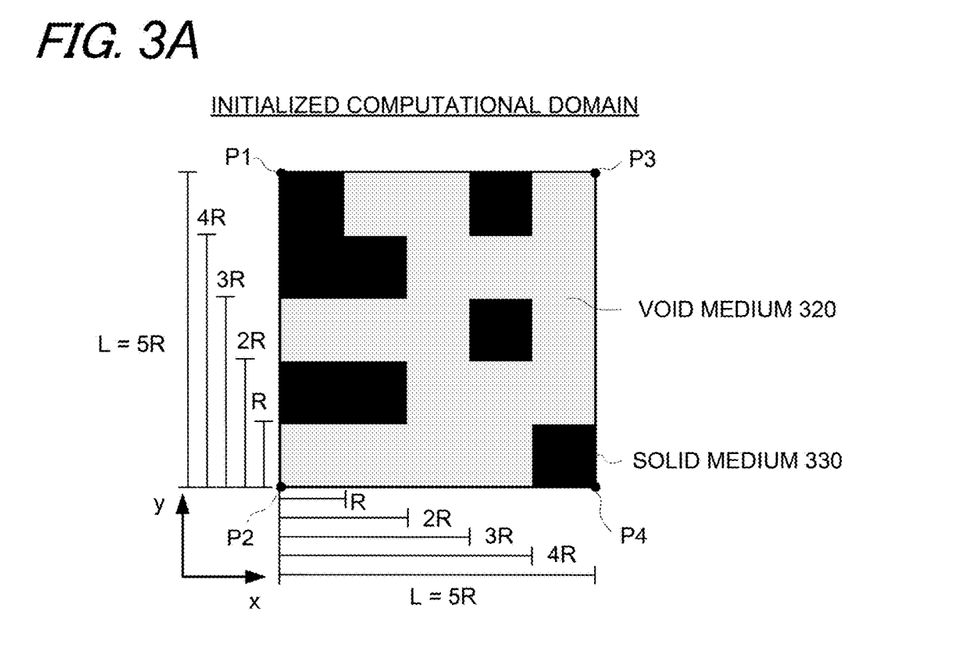
FIG. 3A shows an example of a simplified two-dimensional computational domain.

FIG. 3A shows an illustration of initialized computational domain 200 of the digital rock sample 111, where a number of solid cells represent a solid medium 330 and a number of void cells represent a void medium 320 having fluid molecules according to an example. The initialized computational domain 200 is divided such that all initialized cells 210 have a uniform size slightly smaller than the molecular mean free path of the molecule, but much larger than the molecular size of the fluid molecules. In the case where the molecule is methane, the pores with a size alike to the methane molecule are usually blocked due to adsorption and therefore are negligible in computation of permeability.

The time step 220 is selected such that the average molecular displacement during each time step 220 (i.e. $\Delta t (2k_B T/m)^{1/2}$, where $k_B \approx 1.38\times 10^{-23}$ J/K is the Boltzmann constant and T is the temperature) is smaller than the molecular mean free path. The general rule for selection of the number of cells is to set the cell size $\Delta L$ slightly smaller than the molecular mean free path.

The molecular mean free path $\lambda_0$ is given by:

$$\lambda_0 = \frac{16\mu}{5p_0}\sqrt{\frac{k_B T}{2\pi m}}, \quad \text{Equation 1}$$

where $\mu$ is the dynamic viscosity. The Knudsen number is given by Kn=$\lambda_0$/R, where R is the representative pore size of the shale rock sample 110, and is used to analyze the variation feature of permeability with pressure.

The permeability $\kappa$ is given by:

$$\kappa = \frac{\mu}{(\Delta p_0)/L}\bar{u}, \quad \text{Equation 2}$$

where L is the domain size and $\bar{u}$ is the volumetric velocity component along the driving direction.

The volumetric velocity component $\bar{u}$ is computed by:

$$\bar{u} = \frac{\sum_{j\in void} n_j V_j u_j}{n_0 V_{all}}, \quad \text{Equation 3}$$

where $n_j$ is the number density, $V_j$ is the volume, $u_j$ is the flow velocity component at a void cell j, $n_0$ is the initial uniform density and $V_{all}$ is the total volume of the initialized computational domain 200.

The initial number density $n_0$ is given by:

$$n_0 = p_0/(k_B T). \quad \text{Equation 4:}$$

The permeability $\kappa$ with the detailed volumetric velocity component $\bar{u}$ is given by:

$$\kappa = \frac{\mu}{(\Delta p_0)/L} \frac{\sum_{j \in void} n_j V_j u_j}{n_0 V_{all}}. \qquad \text{Equation 5}$$

Figure 3B:
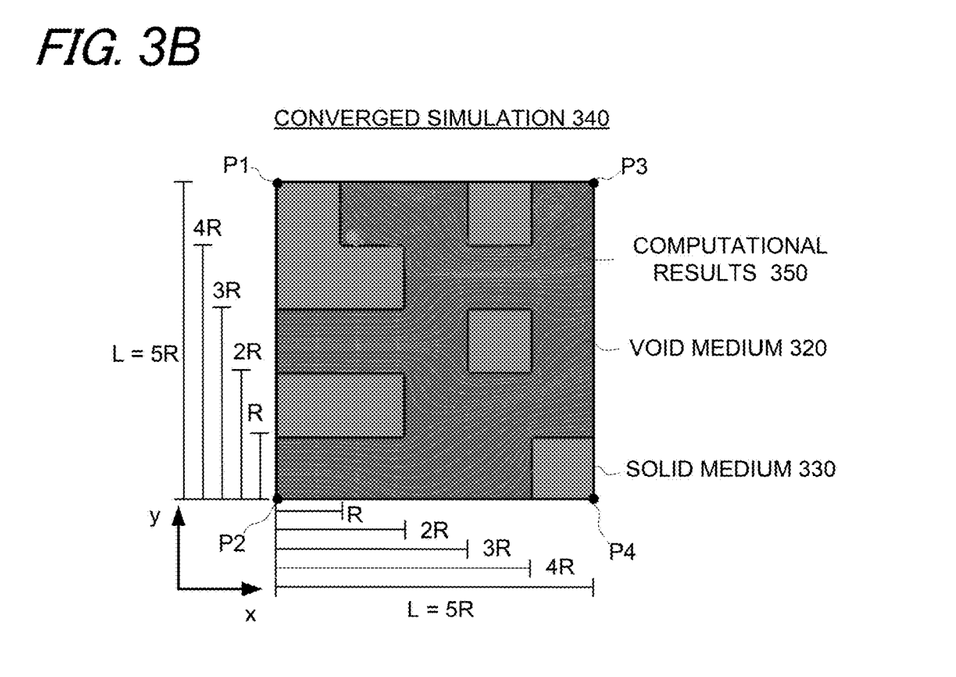
FIG. 3B shows an example of a converged simulation.

FIG. 3B shows an example of a converged simulation 340 including a computational velocity result 350 resulting from applying the DSBGK method further described herein to a benchmark model of the simplified shale rock sample 110 in FIG. 3A. In this case the molecule 230 was methane, R=200 nm, $p_0$=0.4 MPa, $\lambda_0$=12.89 nm, and Kn=0.0644. Therefore, the initialized computational domain 200 is divided into 100×100 initialized cells 210 in the x and y-directions, respectively. The computational velocity result 350 is shown in a graphical format including steady state streamlines indicating the trajectory of the flow.

Figure 4:
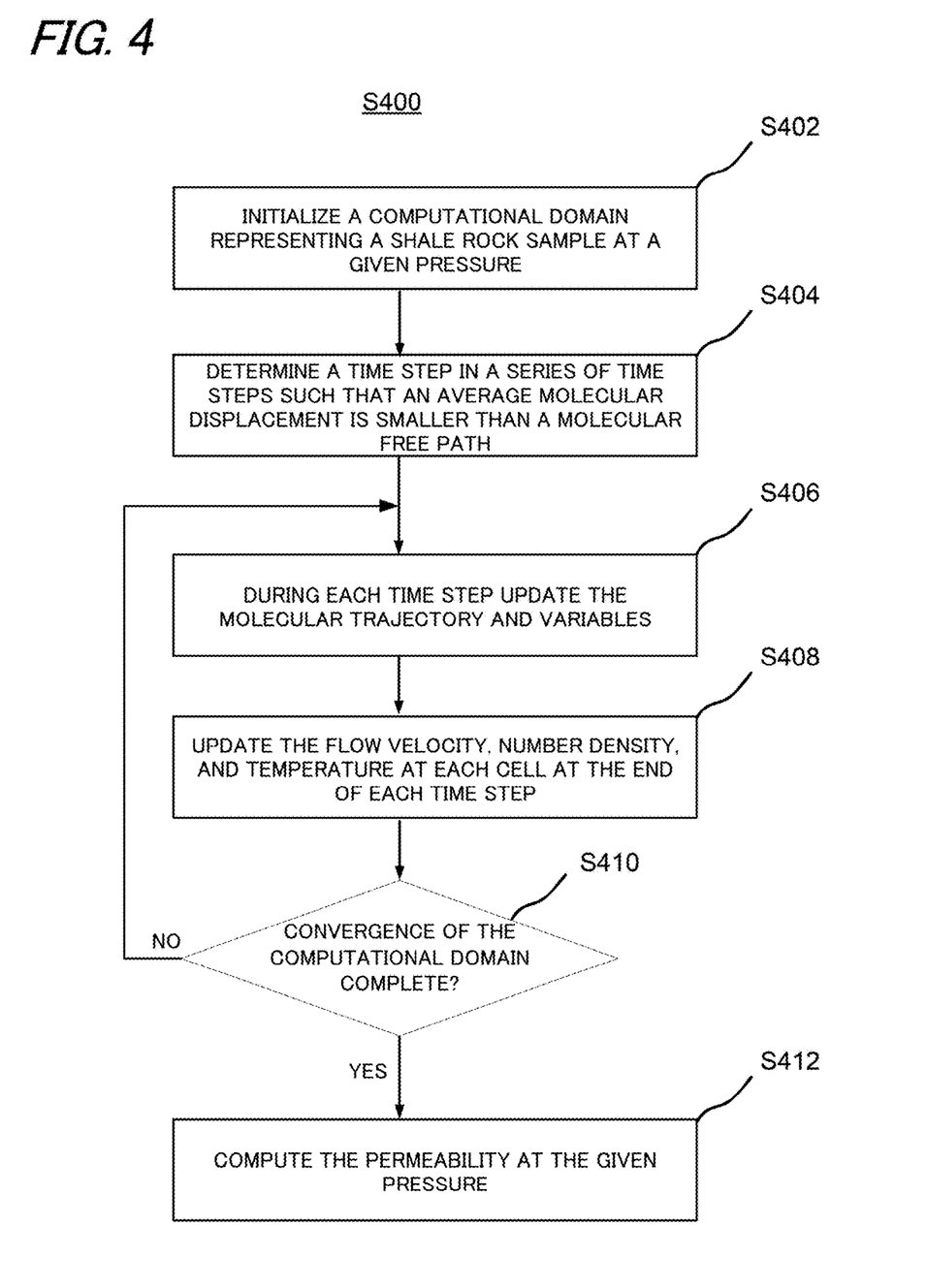
FIG. 4 shows a flow diagram of a Direct Simulation Method Based on Bhatnagar-Gross-Krook Equation (i.e. DSBGK method) to predict the permeability of shale gas in a shale rock sample at a given pressure condition according to an example.

FIG. 4 describes an application S400 of the DSBGK method for simulating the pore-scale gas flow to compute permeability at a given pressure condition by the following steps.

At step S402, the computational domain 200 of the digital rock sample 111 representing the shale rock sample 110 is divided into a number of uniform cells 210. Different values are used in the digital rock sample 111 to represent different material types and correspondingly the cells 210 inside the computational domain 200 have different types, namely solid or void cells. The molecules 230 are randomly distributed inside each void cell 210 and assigned with an initial position, velocity and other molecular variables 231 according to the specified initial probability distribution.

At step S404, the time step 220 is determined where the average molecular displacement during each time step 220 is smaller than the molecular mean free path. Equation 1 is used to calculate the molecular mean free path.

At step S406, during each time step 220 the molecular trajectory and molecular variables 231 are updated. Each molecule 230 will move uniformly and in a straight line before randomly reflecting at the solid cell boundaries 212 according to the diffuse reflection model. A trajectory of each molecule 230 may be divided into several segments by the cell boundary 212. Molecular variables 231 are updated along each segment in sequence at the moving direction. Across the open cell boundaries 212 during each time step 220, the molecules 230 will be removed. New molecules 230 will be generated according to the prescribed pressure at the open cell boundaries 212 at the end of each time step 220.

At step S408, the cell variables 211, including the number density $n_j$, the flow velocity $u_j$, and the temperature $T_j$ for each void cell j 210 are updated. The increments of molecular variables 231 along the segments located inside each void cell j 210 are used to update the cell variables 211 according to the mass, momentum and energy conservation principles of the intermolecular collision process which are simultaneously used to update the molecular variables 231 based on the BGK equation and an extrapolation of the acceptance-rejection scheme.

At step S410, a check if the convergence of the computational domain is complete is done. When the convergence of the computational domain is not complete (NO), steps S406 and S408 of each time step 220 are repeated for the series of time steps 220 until convergence. When the convergence of the computational domain is complete (YES) the process advances to step S412, where the steady state cell variables 211 are used to calculate the permeability according to Equation 5.

Figure 5:
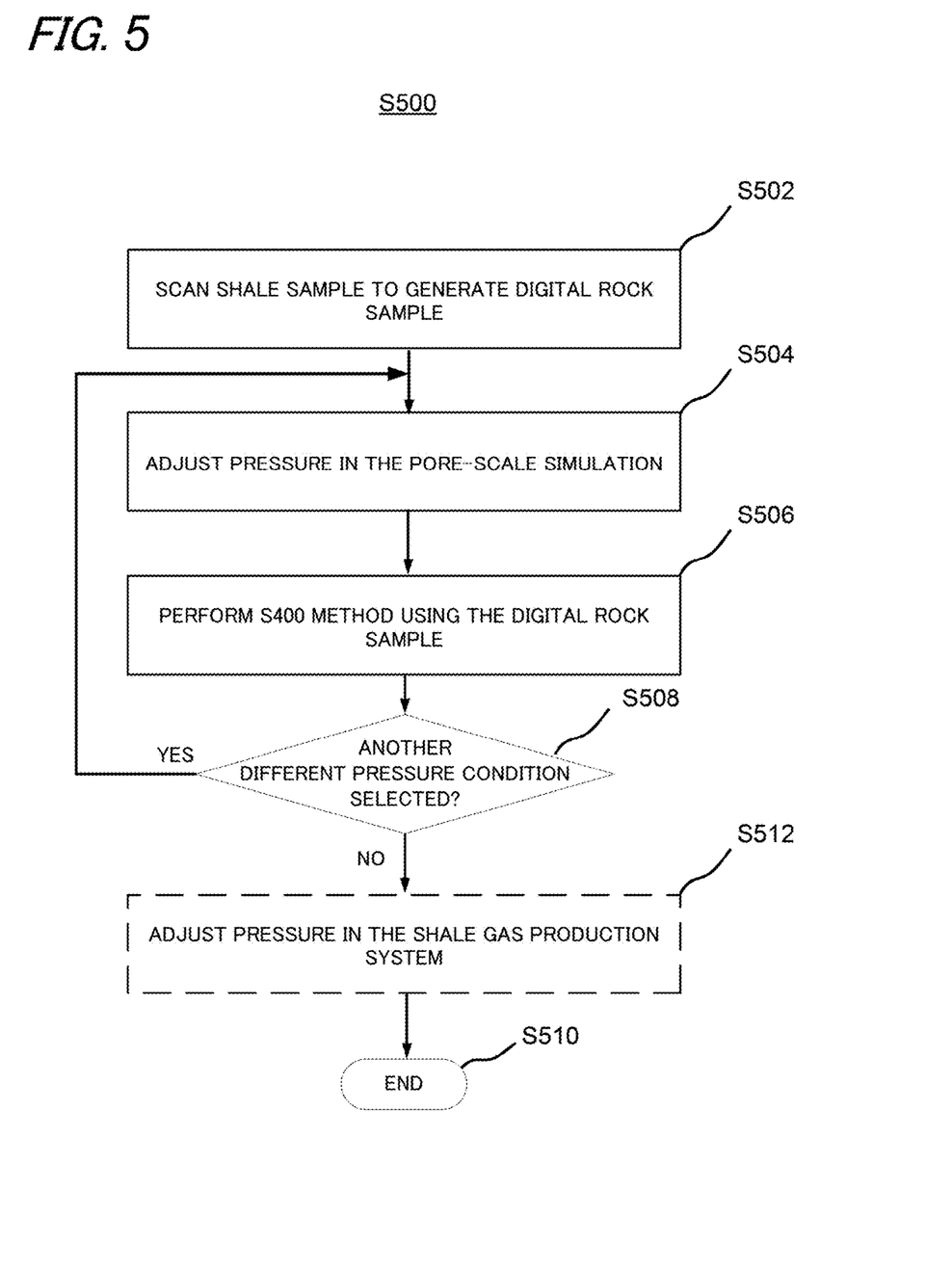
FIG. 5 shows a flow diagram of a method to generate a digital rock sample from a scan of the shale rock sample, to determine the permeability variation with pressure, and optionally, to adjust a pressure used in the shale gas production system using the permeability variation with pressure according to an exemplary embodiment.

FIG. 5 shows a flow diagram of a method S500 to generate the digital rock sample 111 from a scan of the shale rock sample 110, to determine the permeability variation with pressure, and optionally, to adjust a pressure used in the shale gas production system using the permeability variation with pressure according to an exemplary embodiment.

At step S502, the scanner 130 is used to scan the shale rock sample 110 to obtain a digital rock sample 111 for the consequent pore-scale simulations using the method S400. At step S504 an initial pressure is selected. At step S506 the S400 method is performed to predict the permeability of the shale rock sample 110 at the selected pressure condition. At step S508, a check is made if another different pressure condition is selected. When another different pressure condition is selected (YES), steps S504 and S506 are repeated to obtain the permeability at the different pressure condition. Step S508 can be repeated as needed. When another different pressure condition is not selected (NO) the process advances to step S510 and ends. Optionally, when another different pressure condition is not selected (NO) the process advances to step S512 where the pressure applied by the shale gas system 100 is adjusted using the pressure circuitry 108 based on a predicted permeability variation at the different pressure conditions.

Figure 6:
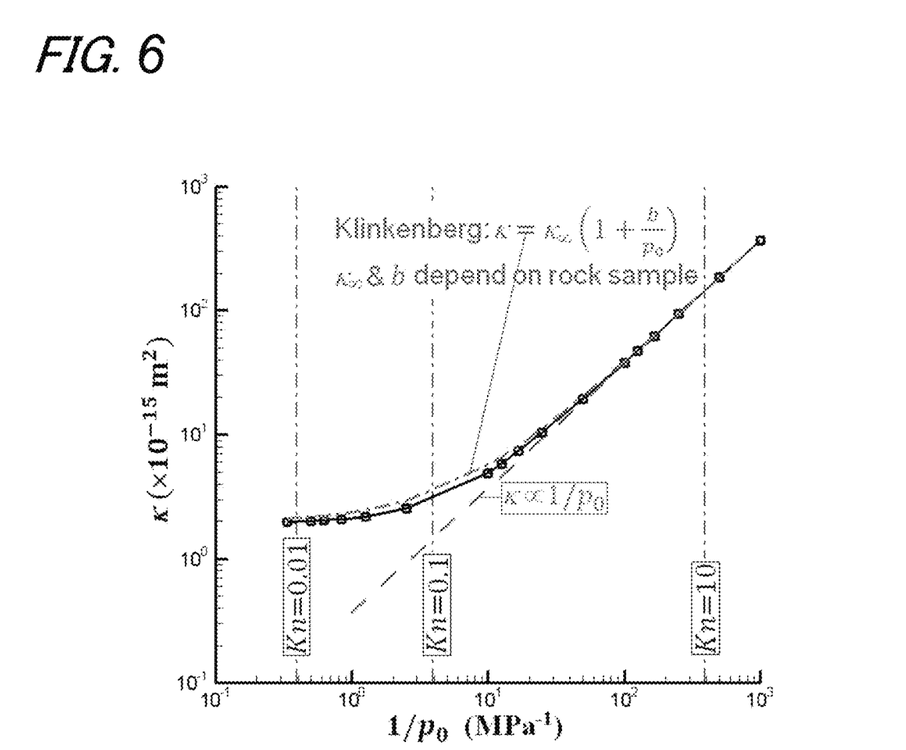
FIG. 6 shows the computational results of permeability in graphical format according to an example.

FIG. 6 is a graph showing the permeability results illustrating the permeability variation with the reciprocal of the pressure. The solid line in the graph represents computed permeability results by the pore-scale simulations. The computed permeability results by the pore-scale simulations shown in this graph can be used to modify the pressure circuitry 108.

Benefits of the inventive system and methods described here can be shown by comparing the production of shale gas with and without adjusting the pressure used in the shale gas production system based on the permeability variation with pressure according to an exemplary embodiment. Numerous modifications and variations of the present disclosure are possible in light of the above teachings. It is therefore to be understood that within the scope of the appended claims, the disclosure may be practiced otherwise than as specifically described herein.

The invention claimed is:

1. A method for enhancing shale gas production from a shale gas well in a shale reservoir with a well rig system, comprising:

scanning a shale rock sample representative of the shale reservoir to create a digital rock sample representing the shale rock sample, wherein the shale rock sample comprises a shale gas comprising fluid molecules, wherein the shale rock sample comprises a solid shale rock matrix having nanopores, wherein the nanopores contain the fluid molecules and the nanopores have a nanopore surface, initializing, on a processor with circuitry, a computational domain representing the digital rock sample at a given pressure condition by dividing the computational domain into a number of cells which are either solid cells or void cells representing the solid shale rock matrix and a void medium representing the nanopores respectively, wherein:

all cells have a uniform size smaller than a molecular mean free path of the fluid molecules and larger than a molecular size of the fluid molecules, each void cell has a number of cell boundaries representing the nanopore surfaces, a number of cell variables, and a number of simulated molecules representative of the fluid molecules having a number of molecular variables, the cell variables of each void cell including a number density, a flow velocity, a representative pore size and a temperature, the molecular variables of each simulated molecule including a spatial position, a molecular velocity, a number of the fluid molecules represented by the simulated molecule, and a distribution function;

determining, on the processor, a time step for a series of time steps such that an average molecular displacement of the simulated molecules is smaller than the molecular mean free path of the simulated molecules, updating, on the processor, the molecular variables during each time step and the cell variables at an end of each time step according to a Direct Simulation Method Based on Bhatnagar-Gross-Krook Equation (DSBGK) method, calculating, on the processor, at completion of all time steps, a permeability of the shale rock sample using a final flow velocity at the given pressure condition, wherein the permeability of the shale rock sample increases proportionally to a viscosity of the fluid molecules, a volumetric velocity of the void cells, and a domain size of the shale rock sample, (ii) the permeability of the shale rock sample decreases proportionally to an amount of pressure difference between two cell boundaries of the void cells, and (iii) the permeability of the shale rock sample is from 0.01 to 0.1 Kn, repeating the calculating with a different initial pressure condition to obtain permeability variations with pressure, and adjusting a pressure of the shale gas in the well rig system to increase production of the shale gas comprising the fluid molecules from the shale reservoir, wherein the well rig system has hydraulics connected to the control circuitry to adjust the pressure of the well rig system based on the permeability variations by accounting for (1) a slippage as a ratio of the molecular mean free path of the fluid molecules present in the shale gas to the representative pore size of the nanopores of the shale rock sample, and (2) an adsorption thickness of the fluid molecules of the shale gas adsorbed on the surfaces of the nanopores in the shale rock sample.

2. The method for enhancing shale gas production from a shale gas well in a shale reservoir of claim 1, wherein the scanning is with a focused ion beam scanning electron microscope or an ultrasonic sensor system.

3. The method for enhancing shale gas production from a shale gas well in a shale reservoir of claim 1, wherein the molecular variables include a distribution function of the molecular weights of the fluid molecules in the shale gas present in the shale rock sample.

4. The method for enhancing shale gas production from a shale gas well in a shale reservoir of claim 1, wherein the molecular variables include a distribution function of the molecular mean free path of the fluid molecules in the shale gas present in the shale rock sample.

5. The method for enhancing shale gas production from a shale gas well in a shale reservoir of claim 1, wherein the scanning is with an ultrasonic sensor system.

* * * * *